(12) United States Patent
Gleim et al.

(10) Patent No.: US 8,216,121 B2
(45) Date of Patent: Jul. 10, 2012

(54) DEVICE FOR GENERATING A PULSED ELECTROMAGNETIC FIELD WITH PULSE CONTROL

(75) Inventors: Peter Gleim, Triesen (LI); Rainer Klopp, Wandlitz (DE)

(73) Assignee: Peter Gleim, Triesen (LI)

( * ) Notice: Subject to any disclaimer, the term of this patent is extended or adjusted under 35 U.S.C. 154(b) by 353 days.

(21) Appl. No.: 12/439,235

(22) PCT Filed: Aug. 24, 2007

(86) PCT No.: PCT/EP2007/058803
§ 371 (c)(1),
(2), (4) Date: Nov. 11, 2009

(87) PCT Pub. No.: WO2008/025731
PCT Pub. Date: Mar. 6, 2008

(65) Prior Publication Data
US 2010/0057146 A1    Mar. 4, 2010

(30) Foreign Application Priority Data
Aug. 28, 2006 (DE) .......................... 10 2006 041 365

(51) Int. Cl.
*A61N 2/04* (2006.01)
(52) U.S. Cl. ................. 600/14; 600/13; 607/72
(58) Field of Classification Search ............ 607/72; 600/13, 14
See application file for complete search history.

(56) References Cited

U.S. PATENT DOCUMENTS

| | | | |
|---|---|---|---|
| 5,800,835 | A | 9/1998 | Zastrow et al. |
| 6,440,059 | B1 | 8/2002 | Haas |

FOREIGN PATENT DOCUMENTS

| | | |
|---|---|---|
| EP | 0 995 463 A1 | 4/2000 |
| GB | 2 295 093 A | 5/1996 |
| JP | 03-277381 | 12/1991 |

OTHER PUBLICATIONS

Rosenspire, et al., Real-Time Control of Neutrophil Metabolism by Very Weak Ultra-Low Frequency Pulsed Magnetic Fields, Biophysical Journal, vol. 88, May 2005, p. 3334-3347.

*Primary Examiner* — Carl H Layno
*Assistant Examiner* — Jeremiah Kimball
(74) *Attorney, Agent, or Firm* — Duane Morris LLP; J. Rodman Steele; Gregory M. Lefkowitz

(57) ABSTRACT

The invention relates to a device for generating a pulsed electromagnetic field with pulse control, wherein the pulses provided by the pulse generator represent periodic pulses having ascending and descending envelope curves with harmonic or anharmonic oscillation profile within the envelope curves, the pulse sequence is in the range of from 1 pulse/20 minutes to 10 pulses/minute, with pulse sequence, pulse function type and electromagnetic flux density being controlled via values which, obtained using non-invasive measuring methods on a target tissue, represent features of the blood microcirculation, with exponential functions as pulse function type being excluded. Greater and longer-lasting improvements of the microcirculation are achieved.

11 Claims, 5 Drawing Sheets

DEVICE FOR GENERATING A PULSED ELECTROMAGNETIC FIELD WITH PULSE CONTROL

The invention relates to a device for generating a pulsed electromagnetic field with pulse control.

A device is known from EP 0 594 655 B1, which device consists of a generator and transmitter and is intended to effect ion transport from intracorporeal electrolyte fluids into and through vessel walls, and in which device the pulsed currents applied have specific properties and, in particular, the amplitudes of the basic pulses correspond to an e-function and a series of pulse sequences is transmitted for 0.3-1 seconds with pauses of 0.7-5 seconds.

EP 0 995 463 B1 claims a device for influencing biological processes in a living tissue, wherein the tissue is exposed to pulses and the amplitude of each single pulse corresponds to a mathematical correlation including the e-function $e^{sin(x \text{ to the power of } b)}$ wherein x is the elapsed time and b is the number of superimposed pulses.

The signal forms generated using well-known devices, which invariably correspond to e-functions, are intended to either improve muscle formation and joint regeneration or stimulate metabolic processes.

The invention is based on the object of providing a device which, by means of specific pulses of a pulsating magnetic field, would allow to improve other features of body functions.

According to the invention, a device for generating a pulsed electromagnetic field with pulse control is provided, said device 10 comprising a pulse generator 12 connected to a coil 14 for generating an electromagnetic field, characterized in that the pulses provided by the pulse generator 12 represent periodic pulses having ascending and descending envelope curves with harmonic or anharmonic oscillation profile within the envelope curves, and that the pulse sequence is in the range of from 1 pulse/20 minutes to 4 pulses/minute, and that the control of pulse sequence, pulse width, pulse function type and electromagnetic flux density is based on measured data which, obtained using non-invasive vital-microscopic, spectrometric, laser-Doppler or oxygen partial pressure measuring methods on a target tissue, represent features of the blood microcirculation, with exponential functions as pulse function type being excluded.

It was found that pulses having e-functions and the described frequency of the pulse sequence of 5 seconds or 3 seconds pause at maximum do have a certain effect on a number of features of the functional state of the microcirculation both in healthy persons and in cases of disease, but this effect has only short and limited influence on the mechanisms of local regulation of the microcirculation, so that long-term prophylactically and therapeutically relevant changes cannot be induced.

Furthermore, it was found that when significantly slowing down the pulse sequence in total, using pulses having no exponentially ascending and descending envelope curves, significantly greater and longer-lasting changes in the features of the microcirculation functional state can be achieved as a result of a significantly stronger direct influence on the local regulatory mechanisms of the microcirculation.

Microcirculation, i.e. the flow of blood cells and blood plasma in extremely small blood vessels (having diameters of <200 μm), is the functionally most important part of the human blood circulation because it is here where the exchange of materials with cells of an organ tissue is effected. This involves supply of oxygen and substrates to cells and removal of metabolic final products. The respective functional state of the microcirculation of an organ determines the regulation width in adapting the microperfusion to changing metabolic requirements and thus the organ function. In addition, unperturbed microcirculation is a precondition for having the initial steps of an immunologic reaction proceed in an unimpeded manner. As a result, the microcirculation has shifted into the focus of clinical-pathophysiological research for quite some time, where the investigation of possible influences on the local regulation of the microcirculation, especially the autorhythmic contractile motions of the vessel wall smooth muscles in arteriolar and venular microvessels (so-called vasomotion), is of particular interest.

The most important criteria used to characterize normal or disturbed microcirculation include:
  the respective state of blood distribution in the microvessel networks;
  the autorhythmic (spontaneous) vessel wall motions in arterioles and venules (vasomotion).
  the stream flow in the arteriolar influx and venular efflux of the capillary networks;
  rheologic features (local hematocrit);
  blood cell flow rates;
  diameter of the microvessels;
  possible accumulation of white blood cells in the region of microcirculation, adhesion to the endothelium and transmigration of white blood cells into tissue.

The vasomotoric functional state substantially determines the width of microcirculation adaptation to changing metabolic requirements and thus the local regulation width of the microcirculation.

According to the invention, measured data from the blood microcirculation are therefore utilized to control the pulses of an electromagnetic field. The measured data are selected from the group consisting of oxygen depletion at the venule side, number of blood cell-perfused nodal points, venular stream flow, local hematocrit in a microvessel, local hematocrit in all microvessels, spontaneous arteriolar vasomotion, state of venular vasomotion, number of adhering white blood cells on a defined venule inner wall, local changes of substance concentrations in a tissue. It is advantageous to utilize a plurality of such features.

The oxygen depletion at the venule side, $\Delta pO_2$, is represented as change in percent compared to the respective initial value at time t=0. What is determined is the absolute difference of oxygen saturation of the hemoglobin in the afferent arterioles and efferent venules in the network of a selected target tissue. Tissue sections of skin or intestine which have the desired blood vessel networks of the organism and, in addition, are part of immunologically active organs and readily accessible to non-invasive measurements, are selected as targets.

As for the number of blood cell-perfused nodal points in a defined microvascular network, nNP, the number of blood cell-perfused branching sites in such a network is used as a measure for the state of blood distribution. $v_{RBC}=80$ μm/s is defined as flow rate limit of red blood cells. Assessment is in + or − (compared to the defined initial value n=60). Borderline cases are scored as +0.5 or −0.5.

The venular stream flow Qven and the arteriolar stream flow Qart are the particle stream flow (blood cell flow) in defined venules and arterioles, respectively. It is given in μm³/s.

The local hematocrit in a blood vessel, also referred to as tube hematocrit $Hc_t$, is the hematocrit in a particular microvessel. It is given as percent change compared to the initial value.

The microcirculation hematocrit, $Hc_{MC}$, is measured in all microvessels with diameters of <200 μm.

The state of arteriolar (or venular) vasomotion, $A_{VM}$, is established by determining the time-motion diagram of the autorhythmic contractile motions of smooth muscle cells of an arteriolar vessel wall (measurement of the distance perpendicular to the microvessel longitudinal axis from an endothelium surface to the opposite endothelium surface at equidistant measurement times; 60 measurements per second; determination of composite oscillations; FOURIER analysis; determination of the amplitude-frequency spectrum). The criterion is the area A under the envelope curve of the amplitude-frequency spectrum of the arteriolar vasomotion (a composite oscillation). The values are given as percent change compared to the initial values.

The number of adhering white blood cells on a defined venule inner wall, nWBC/A, is measured on a defined venule inner surface A=18,000 μm². All those white blood cells adhering to the endothelium longer than 20 seconds are counted.

For example, local changes in concentration of various substances in a tissue are measured for mediators, the ICAM-1 adhesion molecule and others. They are given in relative units of from 0 to 10, where 0 represents "not detected" and the value 10 is assigned to the highest value in a random sample.

The basic principles of measuring such features in human tissues have been described e.g. in Bollinger et al., Microvasc Res 7 (1974), 61-72; Fagrell B, Angiology 23 (1972), 284-298; Fagrell et al., Am J Physiol 233 (1977), H318-321; Wiedemann et al., An Introduction to Microcirculation, Academic Press, NY 1981; and Lancowicz J R (Ed.): Topics in Fluorescence Spectroscopy, Plenum Press, New York, London, Vol. 1-5 (1991-1997), which are incorporated herein by reference.

A parameter-free test method is used for all measured data collected. The WILCOXON rank sum test on a significance level α=5% is put to use. The critical values for T are taken from the literature (Ferguson G, Statistical Analysis in Psychology and Education, McGraw Hill, N.Y. 1959, 318).

The vasomotion is of special importance. It is of prophylactic and therapeutic relevance to influence the disturbed vasomotion so as to obtain a physiological vasomotion rhythm, i.e., impart a physiological vasomotion rhythm in cases of disease. In the event of a disease, the vasomotions of the arteriolar and venular microvessels undergo considerable changes (in most cases significant deceleration; sometimes not more than 1 to 2 vasomotions in the course of several minutes). According to the invention, it is desirable to bring the disturbed vasomotion into the region of physiological vasomotion (about 1-10, especially 1-4 vasomotions per minute). Pathological conditions involving accelerated vasomotion are treated correspondingly.

Accordingly, it was found that, apart from the above-described effects of specific pulsed electromagnetic fields in tissue, it is particularly a change in rhythm of the disturbed spontaneous arteriolar vasomotion that can be achieved, mostly in the sense of stimulating the autorhythmic contractile motions of the vessel wall smooth muscles in extremely small blood vessels (vasomotion of arterioles and venules). When the pulse sequence is changed significantly (slowing down the pulse sequence compared to well-known methods) and when using pulses having no exponentially ascending and descending or abruptly dropping envelope curves, it is possible to effect significantly greater changes in the features of the blood microcirculation.

In clear contrast to well-known methods, wherein blood pressure, respiratory rate or heart rate (macrocirculation) are optionally considered for magnetic field treatment, especially during the treatment itself, the device of the invention uses the above-mentioned specific values of the microcirculation measured particularly prior to treatment as a basis for treatment with extremely low frequencies.

Accordingly, the device according to the invention preferably generates pulse sequences ranging from 1 pulse/10 minutes to 2 pulses/1 minute, more preferably from 1 pulse/5 minutes to 3 pulses/1 minute, especially from 1 pulse/2 minutes to 1 pulse/1 minute. FIGS. 4a and 4b exemplify such advantageous pulse sequences, wherein the intensities are not taken into account.

"Pulse sequence" in the meaning of the invention is understood to be the distance of those oscillation maxima (pulse maxima) from each other which are situated above the intensity baseline in an intensity-time diagram as illustrated in FIG. 4c, for example. If a basic oscillation is present, which can be constant, stochastically different or sinusoidally different in intensity as shown in FIGS. 4d and 4e and 4f, respectively, "pulse sequence" means the distance of those oscillation maxima from each other which are situated markedly above the basic oscillation.

Hence, the pulse sequence is the frequency of maximum magnitudes of the envelope curve occurring per unit time.

Thus, for example, a continuous basic oscillation having an intensity of 80 μT with a pulse width of about 30 μs and a markedly stronger single pulse of 150 μT with a larger pulse width of 0.3 s can be present, the stronger single pulse appearing three to five times per minute. This is also in accordance with the pulse sequence in the meaning of the invention.

Such an arrangement of pulses, i.e. adding a higher-frequency pulse with lower electromagnetic flux density B to the above-mentioned pulse or to the above-mentioned pulse sequence (FIGS. 4a and 4b, respectively) can be advantageous. The additional pulses can vary in their amplitudes (and frequencies) in various ways, as exemplified in FIGS. 4c to 4h. In general, they are around 50 to 80 μT.

Advantageously, the width of a single pulse is around 50 to 300 ms and the width of a basic pulse is around 10 to 60 ms, with 80 to 200 ms and 20 to 40 ms, respectively, being preferred.

In physical terms, the so-called "intensity" or pulse strength is the electromagnetic flux density B in Tesla units.

The pulses generated by the device according to the invention are emitted periodically, representing arc-shaped, such as sinusoidal or cosinusoidal, up to parable-like constructs in their envelope curves in a drawn representation. Within the envelope curves, harmonic oscillations having equal or different amplitudes appear, which may superimpose to form anharmonic oscillations. "Envelope curve" is understood to be the curve which contacts the maxima of amplitudes of different height of a specific sequence of amplitudes, thereby enveloping said sequence in the ascending and descending portions (see FIG. 2). In superimposed anharmonic oscillations this solely relates to the maxima of the adjacent, next higher amplitude.

In a preferred fashion the pulses therefore correspond to a type of function where the ascent and descent of the envelope curves have an approximately arc-shaped profile as in rectified currents.

The pulses are composite oscillations or waves constituted of a multitude of partial oscillations such as harmonic or anharmonic oscillations of varying amplitudes and frequencies, the partial frequencies ranging from ~20 to 3000 Hz.

The envelope curve connects the different amplitudes of the partial oscillations (amplitude=maximum elongation of a partial oscillation). The envelope curve approximately reflects the profile of the composite oscillation or wave.

Particularly preferred is a pulse function type for the envelope curve that corresponds to the type of a rectified cosine current. In the development of a FOURIER series representation of periodic functions such a rectified cosine current is as follows:

$$I(x) = \frac{I_0}{\pi}\left(1 + \frac{\pi}{2}\cos x + \frac{2}{1\cdot 3}\cos 2x - \frac{2}{3\cdot 5}\cos 4x + \frac{2}{5\cdot 7}\cos 6x - + \ldots\right)$$

In a graphic representation it corresponds to FIG. 1c.

"Arc-shaped profile of a curve" is understood to be a curve profile which has no point of inflexion and is negatively curved, such as exemplified in FIGS. 1a, 1b and 1c.

Examples of a superposition of harmonic oscillations and the resulting anharmonic oscillation are presented in FIG. 4.

Optimum treatment results are achieved when the signal (pulse) is varied based on simultaneously measured functional features of the microcirculation. In this respect, it is possible to vary the amplitudes and frequencies of single pulses, pulse sequences or the pulse intervals or intensities. Intensities ranging from nanotesla up to millitesla are possible, e.g. 50 nT to 800 mT, usually being, however, in the microtesla range of about 5-300 µT.

Very good measuring results of biological effects with respect to vasomotion and functional state of the microcirculation are obtained when using electromagnetic flux densities in the range of about 50 µT to about 250 µT, preferably 80 µT to 150 µT. All these magnitudes invariably represent averages.

Compared to varying pulse type and, in particular, pulse sequence, varying the electromagnetic flux density is of lesser importance to the desired effects in the region of the microcirculation.

The device according to the invention can be employed in healthy persons in the sense of improving their performance, in persons exposed to infections and/or stress, in elderly people with restricted physical capability and reduced immune defense, as well as in medical cases. Similarly, the treatment of mammals falls within the scope of the invention. For prophylactic use, i.e. for increasing the physical capability and improving organ functions as a result of expanding the microcirculatory regulation width, it is particularly the effects on vasomotion (feature $A_{VM}$) and state of blood distribution in the microvascular networks (feature nNP) that are of importance.

Compared to devices using e-function pulses and elevated pulse sequences (pulses appear more frequently per unit time), the device according to the invention achieves significantly greater and substantially longer-lasting changes in the features of the microcirculation functional state.

For example, when pulses with e-functions achieve a change of feature $A_{VM}$ of 10% at maximum and the change begins to disappear after about 20 minutes, the signal according to the invention shows a maximum of about 22%, remains at this level for a certain period of time with only a slight drop, and gradually declines at about 50 to 60 minutes. In this way, a markedly improved overall effect is achieved.

The device according to the invention is used with advantage (as a complementary therapy) in various diseases such as impairment of the peripheral circulation, diabetic microangiopathy, diabetic polyneuropathy, impairment of wound and bone healing, as well as ulcerations (such as varicose ulcer in association with chronic venous insufficiency), in multimorbid geriatric patients etc.

The invention will be explained in more detail below with reference to examples. In the appended drawings, FIG. 1a shows an arc-shaped pulse with steep ascent and steep descent;

Figure 1A:
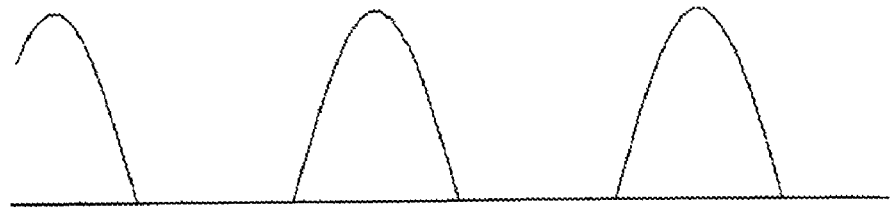
FIG. 1b shows an arc-shaped pulse with gradual ascent and gradual descent.
FIG. 1c shows a rectified cosine current type pulse.
Figure 1B:
Figure 1C:
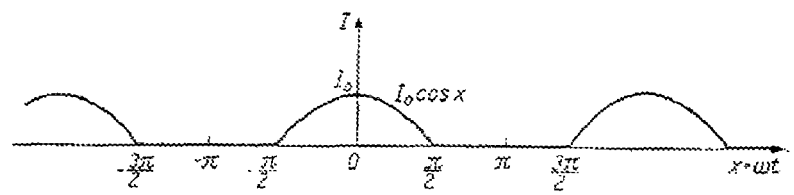
Figure 2:
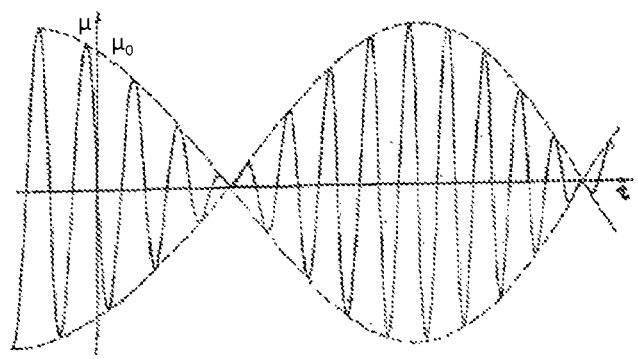
FIG. 2 shows an envelope curve (broken line) of an amplitude-modified wave.
Figure 3:
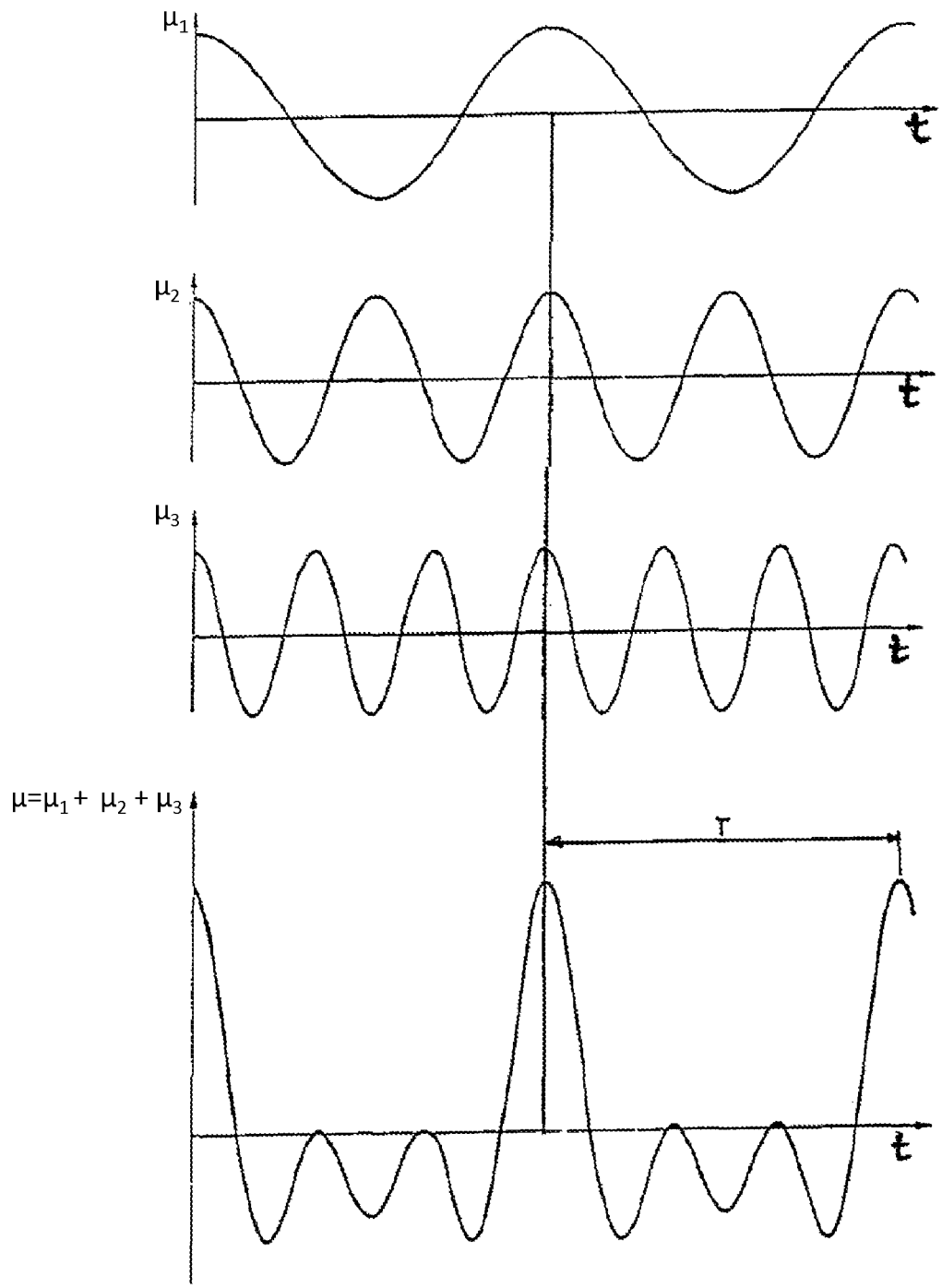
FIG. 3 shows a superposition of three harmonic oscillations $U_1$, $U_2$ and $U_3$ of equal amplitude and phase and a frequency ratio $\omega_1$, $\omega_2$ and $\omega_3$=1:2:3.
Figure 4A:
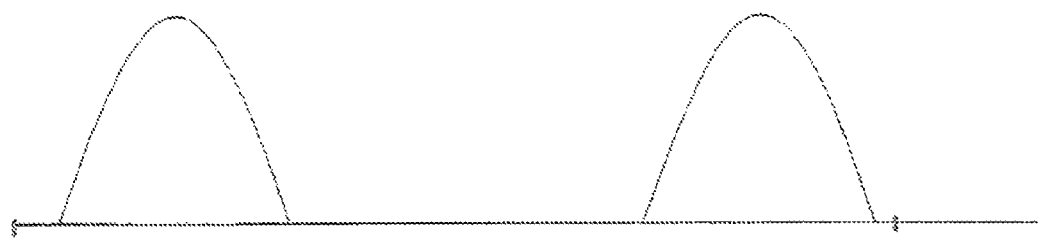
FIG. 4a shows a preferred pulse sequence of 2 per 1 minute.
Figure 4B:
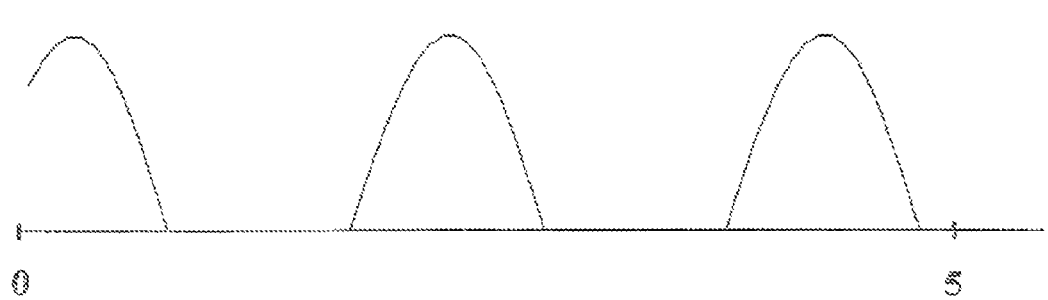
FIG. 4b shows a pulse sequence of 1 per 3 minutes.
Figure 4C:
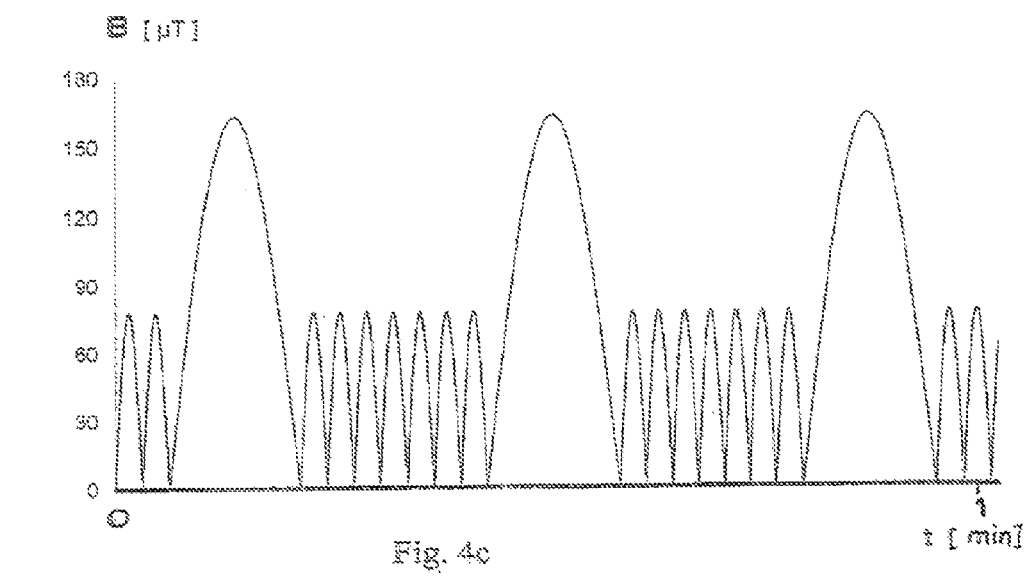
FIG. 4c shows an intensity-time diagram with a pulse sequence of 3 per minute (150 ms and 163 µT), with basic pulses of shorter sequence and low intensity (30 ms and 78 µT)
Figure 4D:
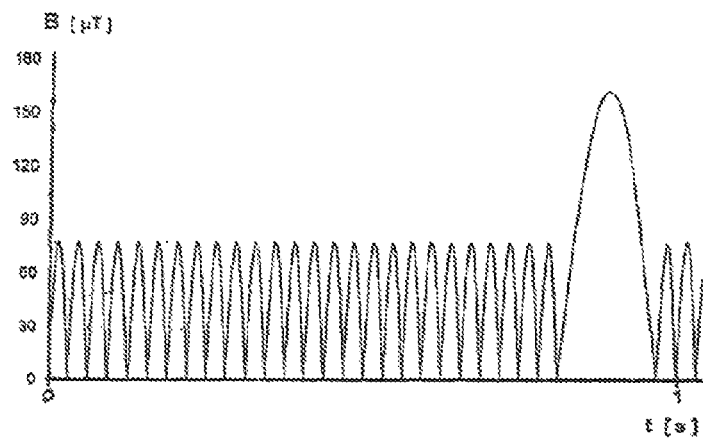
FIG. 4d shows a section of a pulse sequence of 1 pulse per minute (150 ms and 163 µT) with continuous basic pulses (30 ms and 78 µT)
Figure 4E:
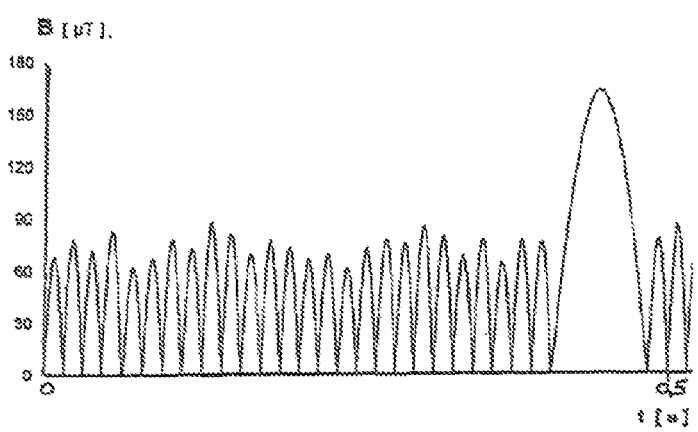
FIG. 4e shows a section of a pulse sequence of 1 pulse per minute with basic pulses having a stochastic intensity profile.
Figure 4F:
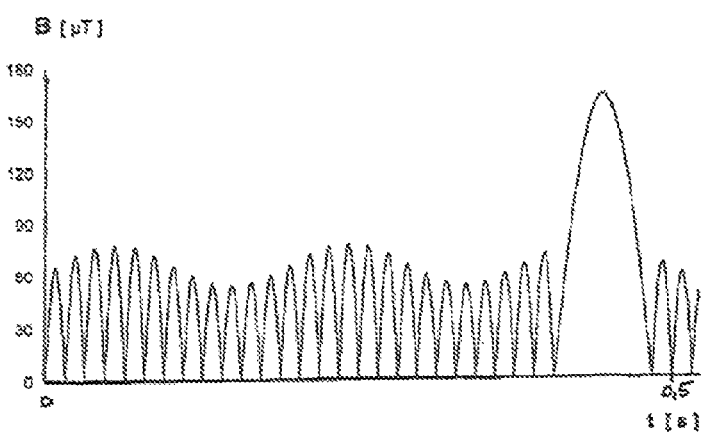
FIG. 4f shows a section of a pulse sequence of 1 pulse per minute with basic pulses having a sinusoidal intensity profile.
Figure 5:
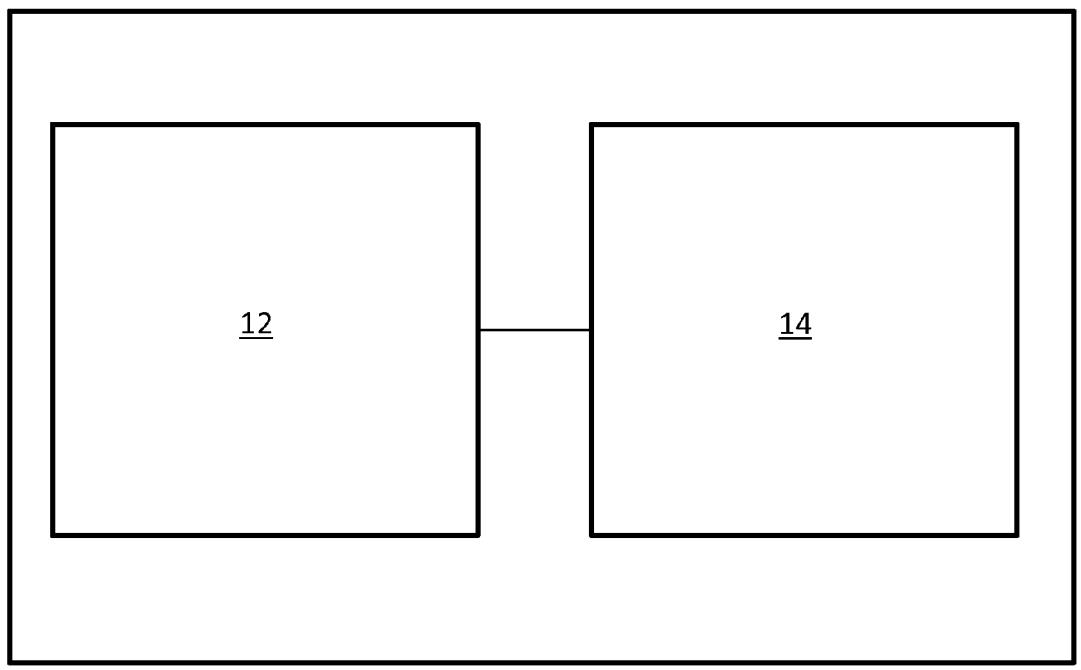
FIG. 5 shows a schematic of a device, including a generator connected to a coil, as described herein.

The pulse widths, being in the range of milliseconds only, are not represented to scale in the figures.

EXAMPLE 1

Using a vital-microscopic investigation set, reflection spectroscopy, laser micro-flow measurement and white-light spectroscopy, representative features of the functional state of the microcirculation were measured in a number of subjects having impaired peripheral circulation:

number of blood cell-perfused nodal points in a defined microvascular network, nNP;

arteriolar vasomotion/area under the envelope curves of the amplitude-frequency spectrum of the arteriolar vasomotion, $A_{VM}$.

Thereafter, a pulse generator is used to generate pulses that are supplied to an electromagnetic coil. The coil is in contact with a skin surface (target tissue). Using this device, pulses are provided to the target tissue at intervals of 1 day, 3 days, 6 days, 9 days and 12 days. Each of the above-mentioned parameters was measured 10 minutes after terminating pulse application.

Number of subjects: 16
Age: 55-65 years
Pulse sequence: 5 per minute
Pulse typ3: approximately rectified sinus
Pulse intensity: single pulse with 180 µT and a pulse width of 150 ms; additional
  basic pulse with 60 µT and a pulse width of 30 ms
  Treatment period: 2×25 minutes at 2 h intervals
  Treatment sequence: each $2^{nd}$ day
  Statistical assessment was performed using the Wilcoxon rank sum test, α=5%.

The percent change for $A_{VM}$ was as high as about 11% on day 3 and increased to about 22% on day 12.

The percent change for nNP was as high as about 10% on day 3 and increased to about 24% on day 12.

COMPARATIVE EXAMPLE 1

The same procedure as in Example 1 was used on a group of 16 subjects.
Pulse sequence: 30 per second
Pulse type: special exponential function $e^{sin(x \text{ to the power of } 3)}$ in accordance with EP 995463
Pulse intensity: 50 μT with a pulse width of 30 ms
Statistical assessment was performed using the Wilcoxon rank sum test, α=5%.
The percent change for $A_{VM}$ was about 3% on day 3 and increased to about 4% on day 12.
The percent change for nNP was about 4% on day 3 and increased to about 6% on day 12.
The above changes do not represent therapeutically relevant changes, revealing that neither pulse type nor pulse sequence has any substantial influence on the local regulatory mechanism of the microcirculation.

EXAMPLE 2

The same procedure as in Example 1 was used on a number of subjects having diabetic microangiopathy.
Number of subjects: 14
Age: 60-70 years
Statistical assessment was performed using the Wilcoxon rank sum test, α=5%.
The percent change for $A_{VM}$ was more than 9% already on day 3 and increased to about 25% on day 12.
The percent change for nNP was as high as about 12% on day 3 and increased to about 30% on day 12.

COMPARATIVE EXAMPLE 2

The same procedure as in Example 2 was used on a group of 14 subjects. Statistical assessment was performed using the Wilcoxon rank sum test, α=5%.
The percent change for $A_{VM}$ was about 5% on day 3 and increased to about 8% on day 12.
The percent change for nNP was also about 5% on day 3 and increased to about 7% on day 12.
The above changes do not represent therapeutically relevant changes, revealing that neither pulse type nor pulse sequence has any substantial influence on the local regulatory mechanism of the microcirculation.

EXAMPLE 3

The same procedure as in Example 1 was used on a number of healthy elderly subjects.
Number of subjects: 16
Age: 55-65 years, no pathological findings
Statistical assessment was performed using the Wilcoxon rank sum test, α=5%.
The percent change for $A_{VM}$ was as high as about 7% on day 3 and increased to about 12% on day 12.
The percent change for nNP was as high as about 8% on day 3 and increased to about 16% on day 12.

COMPARATIVE EXAMPLE 3

The same procedure as in Example 3 was used on a group of 16 subjects. Statistical assessment was performed using the Wilcoxon rank sum test, α=5%.

The percent change for $A_{VM}$ was about 4% on day 3 and increased to about 5% on day 12.
The percent change for nNP was about 5% on day 3 and increased to about 6% on day 12.
The above changes show that the use of such a pulse type and pulse sequence, compared to the use of the device according to the invention, has less influence on the functional state of the microcirculation. The values in Example 3 show an increase by 2 to 3 times at the end of the investigation period.

We claim:

1. A device for generating a pulsed electromagnetic field with pulse control, said device comprising a pulse generator connected to a coil for generating an electromagnetic field, wherein pulses provided by the pulse generator represent periodic pulses having ascending and descending envelope curves with harmonic or anharmonic oscillation profile within the envelope curves, and
   that the pulse sequence is in the range of from 1 pulse/20 minutes to 4 pulses/1 minute, and
   that control of the pulse sequence, pulse width, pulse function type and electromagnetic flux density is based on measured data which, obtained using non-invasive vital-microscopic, spectrometric, laser-Doppler or oxygen partial pressure measuring methods on a target tissue, represent features of the blood microcirculation,
   with exponential functions as pulse function type being excluded.

2. The device according to claim 1, wherein the pulses correspond to a type of function where the ascent and descent of the envelope curves have an arc-shaped profile.

3. The device according to claim 2, wherein the pulse function type for the envelope curve corresponds to the type of a rectified cosine current.

4. The device according to claim 1, wherein the pulse sequence is in the range of from 1 pulse/5 minutes to 3 pulses/1 minute.

5. The device according to claim 1, wherein the pulse control is based on measured data from the blood microcirculation selected from the group consisting of oxygen depletion at the venule side, number of blood cell-perfused nodal points, venular stream flow, local hematocrit in a microvessel, local hematocrit in all microvessels, state of spontaneous arteriolar vasomotion, number of adhering white blood cells on a defined venule inner wall, local changes of substance concentrations in tissue and a plurality of the above features.

6. The device according to claim 5, wherein the pulse control is based on measured data for oxygen depletion at the venule side.

7. The device according to claim 5, wherein the pulse control is based on measured data for the state of spontaneous arteriolar vasomotion.

8. The device according to claim 1, wherein the pulse strength is in the range of from 5 to 300 μT.

9. The device according to claim 1, wherein the pulse sequence is in the range of from 1 pulse/2 minutes to 1 pulse/1 minute.

10. The device according to claim 1, wherein the pulse strength is in the range of from 50 to 250 μT.

11. The device according to claim 1, wherein the pulse strength is in the range of from 80 to 150 μT.

* * * * *